United States Patent [19]

Hamano

[11] 4,240,893
[45] Dec. 23, 1980

[54] DETECTION ELEMENT FOR DETERMINING OXYGEN CONTENT AND DETECTOR FOR DETERMINING OXYGEN CONTENT USING THE SAME

[75] Inventor: Yoshiteru Hamano, Kyoto, Japan
[73] Assignee: Kyoto Ceramic Kabushiki Kaisha, Kyoto, Japan
[21] Appl. No.: 972,895
[22] Filed: Dec. 26, 1978
[51] Int. Cl.³ ............................................. G01N 27/58
[52] U.S. Cl. ................................................. 204/195 S
[58] Field of Search ............................. 204/195 S, 1 S
[56] References Cited
U.S. PATENT DOCUMENTS 3,607,424  9/1971  Maki et al. ................... 204/195 S X
4,152,234  5/1979  Pollner .............................. 204/195 S Primary Examiner—G. L. Kaplan
Attorney, Agent, or Firm—Stuart Lubitz

[57] ABSTRACT

This invention discloses a crack-free and low-cost detection element for determining an oxygen content and a detector for determining an oxygen content using the element. The element comprises a ceramic tubular body, an ion-conductive ceramic bowllike closing member fixed to the opening end of the tubular body in such manner that the opening end of the closing member may not be inserted into the opening of the tubular body, and an inner and an outer electrode respectively mounted on the inside and the outside surface of the bowllike closing member.

8 Claims, 5 Drawing Figures

DETECTION ELEMENT FOR DETERMINING OXYGEN CONTENT AND DETECTOR FOR DETERMINING OXYGEN CONTENT USING THE SAME

BACKGROUND OF THE INVENTION

1. Field of the Invention

This invention relates to a detection element for determining an oxygen content, and more particularly, to a detection element adapted for determining an oxygen content of the hot exhaust gas discharged from an internal combustion engine such as an automobile and to a detector for determining the oxygen content using the element.

2. Prior Art

It is a general practice of the automotive industry to reduce exhaust gas pollution by mounting an exhaust pipe with a detector for determining an oxygen content, and by regulating and maintaining an air fuel ratio at a value of about one. In the conventional detectors of this type it is typical to use a solid electrolyte tubular body as a detection element. Such elements have a tubular body being closed at one end and formed integrally with an ion-conductive ceramic material such as stabilized zirconium oxide. Such elements have serious problems in that ion-conductive ceramic materials, such as zirconium oxide are very high in price.

In contrast thereto, it is proposed in the Japanese Patent Application No. 81027/1975 to provide a detection element whose production cost is reduced by fixing a plate-like stabilized zirconium oxide to the concentric hole formed at the end of a tubular body. The tubular body is formed of an ion-nonconductive ceramic material such as folsterite which is inexpensive. The detection element described that the Japanese Patent Application has the following disadvantages. Namely, (a) the end portion of the element is quickly heated by the hot exhaust gas discharged and a sharp temperature gradient is produced immediately after the start of an internal combustion engine. Because folsterite is inferior in thermal shock resistance to zirconium oxide, the detection element is liable to crack at the end of the folsterite tubular body; (b) the flat zirconium oxide plate fixed to the concentric hole at the end of the folsterite tubular body is greater in the percentage of a catalyzing layer such as platinum on the inside and outside surfaces of the plate than the folsterite tubular body. This plate quickly expanded, with the result that the end portion of the folsterite tubular body is subjected by such expansion to centrifugal depression which, in turn, causes more cracks to occur. Above all, when, as in the previous application, the outer circumferential surface of the flat zirconium oxide plate is mounted on the inner circumference of the opening end of the folsterite tubular body, the likelihood of cracking is great.

OBJECT OF THE INVENTION

A primary object of the invention is to provide a detection element which retains the economical advantages of the detection element disclosed in the above Japanese Patent Application No. 81027/1975 and which can prevent as much as possible the cracking considered as a disadvantage inherent in the element and to provide a detector using the element.

Other objects and advantages of the invention will become more apparent to those skilled in the art from a description given below in conjunction with the accompanying drawings.

DETAILED DESCRIPTION OF THE INVENTION

Figure 1:
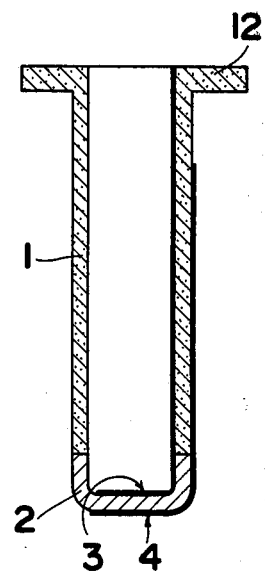
FIGS. 1 through 4 are longitudinal sectional views of different embodiments of the detection element according to the invention.
Figure 3:
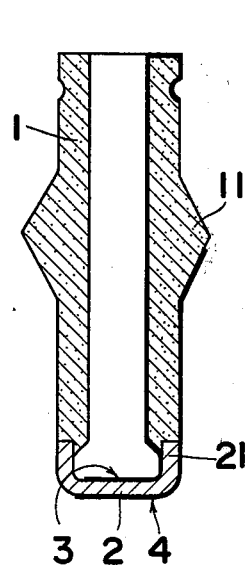
Figure 4:
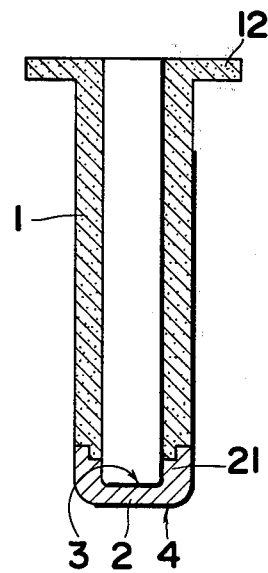

The detection element shown in FIG. 1 is formed such that the opening end of a bowllike closing member 2 is brought into abutment against the opening end of a tubular body having a flange 12 for fixing the element. The element is fixed thereto with suitable sealing glass. According to the embodiment shown in FIG. 2, a tubular body 1 slightly thick-walled and having a similar flange 12 is used and is formed at the outer circumferential edge of the opening end thereof with a stepped groove. A fixing opening 21 of the bowllike closing member 2 is fitted into the groove 21 and is sealed with similar sealing glass. The detection element shown in FIG. 3 is formed of a slightly thick-walled tubular body 1 having generally in the middle thereof an expanded portion 11 for fixing the element. The detection element of FIG. 3 is formed with a stepped groove into which the bowllike closing member 2 is fitted and sealed in the same manner as the embodiment in FIG. 2. FIG. 4 shows a detection element formed such that a stepped groove is formed at the outer circumferential edge of the opening end of a slightly thick-walled tubular body 1 having a flange 12. A stepped groove engaging with the above stepped groove is formed at the inner circumferential edge of the opening 21 of the bowllike closing member 2 so as to connect and seal both openings with sealing glass. In all embodiments illustrated, the inner and outer electrodes 3 and 4 are extended, respectively, to the inside and outside surfaces of the tubular body to facilitate electrical connection, but, in the event that the electrodes 3 and 4 are mounted only on the inside or the outside surface of the member 2, recourse may be had to other suitable means for electrical connection.

The bowllike closing member 2 is made, for example, of an ion-conductive ceramic material such as stabilized zirconium oxide, and the tubular body 1 is made of a ceramic material such as folsterite, alumina, beryllia, having a coefficient of thermal expansion approximate to the above ceramic material making the member 2. The inner electrode 3 and the outer electrode 4 are of a thin layer strip of non-oxidizable metal such as platinum.

As is understood from the embodiments shown in FIGS. 1 through 4, the detection element according to the present invention consists of a tubular body 1 of ceramics, a bowllike closing member 2 of ion-conductive ceramics fixed to the opening end of the tubular body 1, and an inner electrode 3 and an outer electrode 4 mounted to the member 2. The main characteristics of the element are that the bowllike closing member 2 is used and that the fixable opening 21 of the member 2 is fixed in abutment against the opening end of the tubular body 1 without being fitted into the body 1.

When, instead of the platelike closing member used in the prior art element, the bowllike closing member 2 is fixed in abutment against the opening end of the tubular member 1 as proposed by the present invention, the cracking of the tubular body 2 considered as a disadvantage inherent in the prior art element is substantially eliminated. This is believed to be because the end portion of the detection element, which is subjected to rapid heating by exhaust gas to thereby produce a sharp thermal gradient in starting time of an internal combustion engine is made of the bowllike closing member 2 of zirconium oxide. This material is high in thermal shock resistance. Cracking is also prevented because the tubular body 1 is made of a material low in thermal shock resistance such as folsterite which is gradually heated by heat conduction from the member 2.

Furthermore, a means for bringing about a synergic effect in preventing cracking has been disclosed which relates to the way member 2 is fixed to the body 1. The bowllike closing member 2 is fixed, not by inserting the member 2 into the opening of the tubular body 1, but by fixing the former to the latter in abutment against the latter. In this manner even if the member 2 is quickly heated and expanded at the time the engine is started, the tubular body 1 is not heavily subjected to centrifugal depression by the expansion of the member 2. Moreover, since the bowllike closing member 2 made of the more expensive zirconium oxide is very small in percentage member 2 occupies out of the whole detection element, the element of the invention retains the advantage possessed by the prior art.

Figure 2:
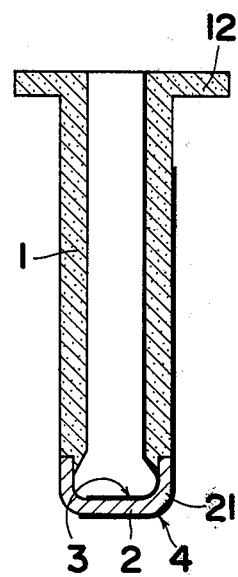

As seen in FIGS. 2 and 4, when a stepped groove is formed at the circumferential edge of the opening end of the tubular body 1 and the bowllike closing member 2 is fitted in the groove and fixed thereto, there is additional advantage that coaxial fixing of both the member 2 and the body 1 improves workability. Furthermore, the element of the invention has another advantage in that the provision of the stepped groove at the outer circumferential edge of the end portion reduces the area which is exposed to the heat of the glass sealed portion which is low in heat resistance. Accordingly, the groove structurally protects the sealed portion against thermal damage.

Thus, the detection element of the invention is an improved invention designed to prevent the cracking of the element while it retains the economic advantages of the prior art detection element. It is believed to be very useful in the automotive industry and other related industries.

A description will now be given of a detector for determining an oxygen content using the detection element of the invention described above with reference to FIG. 5. The reference character A in the figure designates a detection element of the type shown in FIG. 3. The detection element A is supported on its expanded portion 11 from below by a sealing member 6 for the prevention of gas leakage and is depressed from above and retained by a fixing means 5. Fixing means 5 is made up of a ringlike washer 51 and a compression spring 52 and is incorporated in a casing 8. Electrical connection between the inner electrode 3 of the detection element A and the outside is secured by an electrical connection means 7 made up of a metal lead cap 71 fitted over the upper end opening of the element A and a cylindrical metal lead terminal 72 mounted to the cap 71.

The outer electrode 4 is conducted to the metal casing 8 by the sealing member 6. Sealing member 6 has a dual function in that it acts as the electrical connection means 7. It is electrically grounded by the casing 8 and maintained at zero potential.

The casing 8 is made up of an upper casing 81 and a lower casing 82 having opposing flanges 811 and 821, respectively. Both casings are integrally connected in the flanges 811 and 821 by suitable fasteners. Furthermore, an insulating bush 9 is fitted in a hole in the upper end face of the upper casing 81 for inserting a lead terminal through the hole so as to prevent the lead terminal 9 and the upper casing 81 from coming into contact with each other thereby causing a short-circuit. In addition thereto, in the detector illustrated, a heat-resisting member 10 such as heat-proof wool is stuffed between the lower casing 82 and the tubular body 1 of the detection element. This helps prevent the tubular body 1 of the element which is low in thermal shock resistance from coming into direct contact with hot exhaust gas flowing in from gas vent pores 822 of the lower casing 82, and from being quickly heated by direct contact with the lower casing. Such configuration also gives heat screening effect to the glass sealed portion between the tubular body 1 and the bowllike closing member 2.

Since the detector of the construction described above uses the described type detection element of the invention as a detection element and, if necessary, the heat resisting member 10, the detector is believed to be free from problems such as cracking. It is also easy to reduce the production cost. In addition to such marked effects, the detector of the invention provides advantages such as (a) vibration resistance is greatly increased by the employment of the ringlike washer 51 and compression spring 52 as a fixing means 5 for the detection element A; and (b) the electrically conductive members heretofore incorporated in large numbers into the detection element are eliminated by the use of the lead cap 71, lead terminal 72 and electrically conductive sealing member 6. Thus, the detector structurally is simplified and reduced in the number of manufacturing steps.

Figure 5:
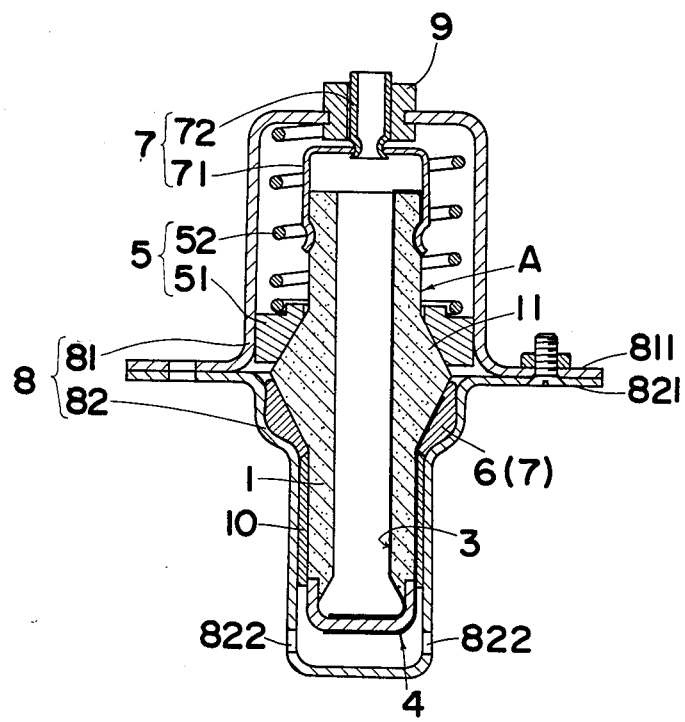
FIG. 5 is a longitudinal sectional view of one embodiment of the detector according to the invention.

As will be understood from the embodiment illustrated in FIG. 5, the detector of the invention is of simple construction in that it comprises detection element A of the invention having an inner electrode 3 and an outer electrode 4, a fixing means 5 for the element A, preferably a gas leak preventing means 6, an electrical connection means for the electrodes 3 and 4, and a casing 8 for containing the preceding members and means therein, and preferably the aforementioned heat-resisting member 10. Thus, the detector obviates those problems, due to the detection element itself and to shock, and makes it easy to reduce the production cost of the detector, a great contribution to the automotive industry.

It should be understood that the detection element and the detector of this invention are not limited to the embodiments described and illustrated, and that various modifications may be made without departing from the scope of the invention.

What we claim is:

1. A detection element for determining an oxygen content in an environment subjected to rapid temperature changes, such as are encountered in the testing of exhaust gases from an internal combustion engine, comprising:

a ceramic tubular body having an open end with a stepped surface formed on the outer circumferential edge thereof;

an ion-conductive ceramic closing member having high thermal shock resistance fixed to said open end of the tubular body, wherein said closing member is substantially bowl-like in shape and fits over the end of the tubular body in engagement with the stepped surface, said closing member being glass sealed to the tubular body, whereby when the detection element is exposed to a sharp thermal gradient the expansion of the closing member will exert minimal pressure on the tubular body and the glass seal will be protected from heat by the closing member; and an inner and outer electrode respectively mounted on the inside and outside surface of the closing member.

2. A detection element according to claim 1 wherein the open end of said bowllike closing member is formed at the inner circumferential edge thereof with a stepped groove engaging with said stepped groove of the tubular body, and both said stepped grooves are engaged with each other and glass sealed.

3. A detection element according to claim 1 wherein said tubular body is provided in substantially the middle thereof with an expanded portion.

4. A detection element according to claim 1 wherein said tubular body is provided at the rear end thereof with a flange.

5. A detection element according to claim 1 wherein said bowllike closing member is made of stabilized zirconium oxide and said tubular body is made of a ceramic material having a coefficient of thermal expansion approximately equal to the coefficient of thermal expansion of said zirconium oxide.

6. The detection element of claim 1 in combination with:

a casing within which said detection element is secured, said casing including a hollow tubular section within which said detection element is located, said tubular section including at least one gas vent located at an end thereof for exposing the closing member to gases in the environment; and a heat resisting member located between the wall of the casing and the tubular body to thereby prevent hot gases from coming into direct contact with the tubular body of the detection element.

7. The apparatus of claim 6 wherein the heat resisting member is a wool sheath.

8. The apparatus of claim 6 wherein the detection element includes an expanded portion in the middle of the tubular portion and is secured in a fixed position within the casing by means of a compression spring which surrounds the rear of the tubular portion and is biased against the rear of the casing and the expanded portion.

* * * * *